US011555047B2

(12) United States Patent
D'Antonio et al.

(10) Patent No.: US 11,555,047 B2
(45) Date of Patent: Jan. 17, 2023

(54) ONE-STEP SYNTHESIS OF PHOSPHATE-BASED INHIBITORS AND APPLICATIONS THEREOF

(71) Applicants: UNIVERSITY OF SOUTH CAROLINA, Columbia, SC (US); NORTH CAROLINA STATE UNIVERSITY, Raleigh, NC (US)

(72) Inventors: Edward D'Antonio, Bluffton, SC (US); Joshua Pierce, Raleigh, NC (US)

(73) Assignees: University of South Carolina, Columbia, SC (US); North Carolina State University, Raleigh, NC (US)

( * ) Notice: Subject to any disclaimer, the term of this patent is extended or adjusted under 35 U.S.C. 154(b) by 209 days.

(21) Appl. No.: 17/005,917

(22) Filed: Aug. 28, 2020

(65) Prior Publication Data
US 2021/0130381 A1 May 6, 2021

Related U.S. Application Data

(60) Provisional application No. 62/928,727, filed on Oct. 31, 2019.

(51) Int. Cl.
*C07F 13/00* (2006.01)
*C07F 9/09* (2006.01)

(52) U.S. Cl.
CPC ............... *C07F 13/00* (2013.01); *C07F 9/09* (2013.01)

(58) Field of Classification Search
None
See application file for complete search history.

(56) References Cited

U.S. PATENT DOCUMENTS

| | | | |
|---|---|---|---|
| 4,761,404 A | 8/1988 | Bugianesi et al. | |
| 5,763,470 A | 6/1998 | Tang et al. | |
| 6,551,600 B2 | 4/2003 | Hawkins et al. | |
| 6,723,710 B2 | 4/2004 | Christianson et al. | |
| 8,618,080 B2 | 12/2013 | Bauer et al. | |
| 9,956,240 B2 | 5/2018 | D'Antonio et al. | |
| 10,682,359 B2 | 6/2020 | D'Antonio | |
| 2008/0091005 A1* | 4/2008 | Wang | C07H 21/04 536/26.6 |
| 2017/0145042 A1 | 5/2017 | D'Antonio | |
| 2018/0155373 A1 | 6/2018 | D'Antonio | |

FOREIGN PATENT DOCUMENTS

WO    WO 00/35944    6/2000

OTHER PUBLICATIONS

McMurry "Organic Chemistry, Fourth Edition" Brooks/Cole Publishing Company, 1996, p. 831.*
Albler, et al. "Synthetic Routes towards Fluorine-Containing Amino Sugars: Synthesis of Fluorinated Analogues of Tomosamine and 4-Amino-4-deoxyarabinose" *Eur. J. Org. Chem.* 2014 (2014) pp. 2451-2459.
Andriani, et al. "Activity in vivo of anti-Trypanosoma cruzi compounds selected from a high throughput screening" *PLoS Negl. Trop. Dis.* 5:e1298 (2011) pp. 1-6.
Bakker, et al. "Compartmentation protects trypanosomes from the dangerous design of glycolysis" *PNAS* 97 (1999) pp. 2087-2092.
Barrett, et al. "The trypanosomiases" *Lancet* 362 (2003) pp. 1469-1480.
Bern, et al. "*Trypanosoma cruzi* and Chagas' disease in the United States" *Clin. Microbiol. Rev.* 24 (2011) pp. 655-681.
Buechner, et al. "The crystal structure of glucokinase from *Leishmania braziliensis*" *Mol. Biochem. Parasitol.* 227 (2019) pp. 47-52.
Cáceres, et al. "Molecular and biochemical characterization of hexokinase from *Trypanosoma cruzi*" *Mol. Biochem. Parasitol.* 126 (2003) pp. 251-262.
Calamini, et al. "Small Molecule Proteostasis Regulators for Protein Conformational Diseases" *Nat. Chem. Biol.* 8 (2012) pp. 185-196.
Cançado, J.R. "Long term evaluation of etiological treatment of Chagas disease with benznidazole" *Rev. Inst. Med. Trop. S. Paulo* 44 (2002) pp. 29-37.
Cazzulo, J.J. "Aerobic fermentation of glucose by trypanosomatids" *FASEB J.* 6 (1992) pp. 3153-3161.
CDC. "Neglected Parasitic Infections in the United States: Chagas Disease" *Ctrs. Dis. Contr. Prev.* (2018) pp. 1-4. http://www.cdc.gov/parasites/chagas/.
CDC. "Parasites—Leishmaniasis: Biology" *Ctrs. Dis. Contr. Prev.* (2018) p. 1. https://www.cdc.gov/parasites/leishmaniasis/biology.

(Continued)

*Primary Examiner* — Joseph R Kosack
(74) *Attorney, Agent, or Firm* — Dority & Manning, P.A.

(57) ABSTRACT

One-step methods for forming phosphate-based enzyme inhibitors are disclosed. Methods include reacting o-phosphorylethanolamine with an acyl chloride at acidic conditions. Acyl chlorides can be derivatized. The phosphate-based enzyme inhibitors can inhibit enzymes of the pentose phosphate pathway including D-ribose-5-phosphate aldose-ketose isomerase enzymes such as *T. cruzi* ribose 5-phosphate isomerase type B and D-ribulose-5-phosphate 3-epimerase enzymes. Methods can be used in forming pharmaceutical compositions for use in treatment of disease caused by kinetoplastid parasites including *T. cruzi, T. brucei,* and *Leishmania* spp.

12 Claims, 6 Drawing Sheets

Specification includes a Sequence Listing.

(56) References Cited

OTHER PUBLICATIONS

Chauvlac, et al. "Crystal structure of reduced MsAcg, a putative nitroreductase from *Mycobacterium smegmatis* and a close homologue of *Mycobacterium tuberculosis* Acg" *J. Biol. Chem.* 287 (2012) pp. 44372-44383.

Cordiero, et al. "The crystal structure of *Trypanosoma cruzi* glucokinase reveals features determining oligomerization and anomer specificity of hexo-phosphorylating enzymes" *J. Mol. Biol.* 372 (2007) pp. 1215-1226.

Croft, et al. "Chemotherapy of trypanosomiases and leishmaniasis" *Trends Parasitol.* 21 (2005) pp. 508-512.

D'Abusco, et al. "A peptidyl-glucosamine derivative affects IKKα kinase activity in human chondrocytes" *Arth. Res. Ther.* 12:R18 (2010) pp. 1-11.

D'Antonio, et al. "Structure-based approach to the identification of a novel group of selective glucosamine analogue inhibitors of *Trypanosoma cruzi* glucokinase" *Mol. Biochem. Parasitol.* 204 (2015) pp. 64-76.

Doerig, C. "Protein kinases as targets for anti-parasitic chemotherapy" *Biochim. et Biophys. Acta* 1697 (2004) pp. 155-168.

Engel, et al. "Aerobic glucose fermentation by *Trypanosoma cruzi* axenic culture amastigote-like forms during growth and differentiation to epimastigotes" *Mol. Biochem. Parasitol.* 26 (1987) pp. 1-10.

Fatome, et al. "Radioprotective effects of Δ³-chromenes substituted in 3 by an electro-attractive group (translated)" *Eur. J. Med. Chem. Chimica Therapeutica* 11 (1976) pp. 81-82.

Gallo-Ebert, et al. "Novel Antifungal Drug Discovery Based on Targeting Pathways Regulating the Fungus-Conserved Upc2 Transcription Factor" *Antimicrob. Agent Chemother.* 58 (2014) pp. 258-266.

Gibson, et al. "Affinity labeling and characterization of the active site histidine of glucosephosphate isomerase. Sequence homology with triosephosphate isomerase" *J. Biol. Chem.* 255 (1980) pp. 9369-9374.

Habib, et al. "Catalyst-free 1, 3-dipolar cycloaddition of 3-nitrochromen with sodium azide: a facile method for the synthesis of 4-aryl-1,4-dihydrochromeno [4,3-d] [1,2,3] triazole derivatives" *Tetrahedron* 65 (2009) pp. 5799-5804.

Hall, et al. "Activation of benznidazole by trypanosomal type 1 nitroreductases results in glyoxal formation" *Antimicrob. Agents Chemother.* 56 (2012) pp. 115-123.

Hartman, et al. "Inactivation of class I fructose diphosphate aldolases by the substrate analog N-bromoacetylethanolamine phosphate" *J. Biol. Chem.* 248 (1973) pp. 8233-8239.

Herwaldt, et al. "Characteristics of patients for whom benznidazole was released through the CDC-sponsored investigational new drug program for treatment of Chagas disease—United States, 2011-2018" *Morb. Mortal. Wkly. Rep.* 67 (2018) pp. 803-805.

Heussler, et al. "Hijacking of Host Cell IKK Signalosomes by the Transforming Parasite *Theileria*" *Science* 298 (2002) pp. 1033-1036.

Igoillo-Esteve, et al. "The pentose phosphate pathway in *Trypanosoma cruzi*: a potential target for the chemotherapy of Chagas disease" *Ann. Braz. Aca. Sci.* 79 (2007) pp. 649-663.

Ito, et al. "Identification of novel selective P2Y6 receptor antagonists by high-throughput screening assay" *Life Sci.* 180 (2017) pp. 137-142.

Jäger, et al. (Eds.) "Trypanosomatid diseases: molecular routes to drug discovery" vol. 4 *Wiley-Blackwell* (2013) pp. 1-555.

Karlsson, et al. "Separation of monosaccharides by hydrophilic interaction chromatography with evaporative light scattering detection" *J. Chromatogr. A* 1092 (2005) pp. 246-249.

Lefebvre, et al. "Mononucleoside phosphotriester derivatives with S-acyl-2-thioethyl bioreversible phosphate-protecting groups: Intracellular delivery of 3'-azido-2',3'-dideoxythymidine 5'-monophosphate" *J. Med. Chem.* 38 (1995) pp. 3941-3950.

Ling, et al. "A method for fast shot boundary detection based on SVM" *IEEE Cong. Image Sign. Proc.* 2 (2008) pp. 445-449.

Lipinski, et al. "Experimental and computational approaches to estimate solubility and permeability in drug discovery and development settings" *Adv. Drug Deliv. Rev.* 46 (2001) pp. 3-26.

Lipinski, et al. "Experimental and computational approaches to estimate solubility and permeability in drug discovery and development settings" *Adv. Drug Deliv. Rev.* 23 (1997) pp. 3-25.

Lobo-Rojas, et al. "*Trypanosoma cruzi* contains two galactokinases; molecular and biochemical characterization" *Parasitol. Int'l* 65 (2016) pp. 472-482.

Luzina, et al. "Synthesis, evaluation of anticancer activity and COMPARE analysis of N-bis(trifluoromethyl)alkyl-N'-substituted ureas with pharmacophoric moieties" *Eur. J. Med. Chem.* 53 (2012) pp. 364-373.

Malo, et al. "Statistical practice in high-throughput screening data analysis" *Nat. Biotechnol.* 24 (2006) pp. 167-175.

Mao, et al. "A Novel Chromene-Based Pan-PI3 Kinase Inhibitor Displays Preclinical Activity in Leukemia and Myeloma" *Blood* 112 (2008) pp. 568-569. (Abstract only).

Meija, et al. "Benznidazole-resistance in *Trypanosoma cruzi* is a readily acquired trait that can arise independently in a single population" *J. Infect. Dis.* 206 (2012) pp. 220-228.

Mercaldi, et al. "Discovery of antichagasic inhibitors by high-throughput screening with *Trypanosoma cruzi* glucokinase" *Bioorg. Med. Chem. Lett.* 29 (2019) pp. 1948-1953. (Abstract only).

Milanes, et al. "Enzymatic and structural characterization of the *Naegleria fowleri* glucokinase" *Antimicrob. Agents Chemother.* 63 (2019) pp. e02410-e02418.

Rahmani-Nezhad, et al. "Synthesis, in vitro cytotoxicity and apoptosis inducing study of 2-aryl-3-nitro-2H-chromene derivatives as potent anti-breast cancer agents" *Eur. J. Med. Chem.* 86 (2014) pp. 562-569.

Rassi, et al. "Challenges and opportunities for primary, secondary, and tertiary prevention of Chagas' disease" *Heart* 95 (2009) pp. 524-534.

Ruda, et al. "Aryl phosphoramidates of 5-phospho erythronohydroxamic acid, a new class of potent trypanocidal compounds" *J. Med. Chem.* 53 (2010), pp. 6071-6078.

Ruda, et al. "Synthesis and biological evaluation of phosphate prodrugs of 4-phospho-Derythronohydroxamic acid, an inhibitor of 6-phosphogluconate dehydrogenase" *ChemMedChem,* 2 (2007) pp. 1169-1180.

Sánchez-Valdéz, et al. "Spontaneous dormancy protects *Trypanosoma cruzi* during extended drug exposure" *eLife* 7:e34039 (2018) pp. 1-20.

Stern, et al. "Structures of type B ribose 5-phosphate isomerase from Trypanosoma cruzi shed light on the determinants of sugar specificity in the structural family" *FEBS J.* 278 (2011) pp. 793-808.

Stern, et al. "Ribose 5-phosphate isomerase type B from *Trypanosoma cruzi*: kinetic properties and site-directed mutagenesis reveal information about the reaction mechanism" *Biochem. J.* 401 (2007) pp. 279-285.

Tielens, et al. "Differences in energy metabolism between trypanosomatidae" *Parasitol. Today* 14 (1998) pp. 265-271.

Urbina, et al. "Specific chemotherapy of Chagas disease: controversies and advances" *Trends Parasitol.* 19 (2003) pp. 495-501.

Who. "Chagas disease (also known as American trypanosomiasis)" *World Health Organization* (2020) https://www.who.int/news-room/fact-sheets/detail/chagas-disease-(american-trypanosomiasis).

Wilson, et al. "Sequencing, Modeling, and Selective Inhibition of Trypanosoma brucei Hexokinase" *Chem. Bio.* 9 (2002) pp. 839-847.

Yin, et al. "Preparation of S14161 and its analogues and the discovery of 6-bromo-8-ethoxy-3-nitro-2H-chromene as a more potent antitumor agent in vitro" *Bioorg. Med. Chem. Lett.* 23 (2013) pp. 3314-3319.

Zhang, et al. "An improved method of amide synthesis using acyl chlorides" *Tetrahedron Lett.* 50 (2009) pp. 2964-2966.

\* cited by examiner

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catatgacgc gccgagtcg                                                  19

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcgagcctg tacatcattt ctcg                                            24
```

```
<210> SEQ ID NO 3
<211> LENGTH: 21
<212> TYPE: PRT
<213> ORGANISM: Trypanosoma cruzi

<400> SEQUENCE: 3

Val Leu Ala Cys Gly Ser Gly Ile Gly Met Ser Ile Ala Ala Asn Lys
1               5                   10                  15

Val Pro Gly Val Arg
            20
```

ONE-STEP SYNTHESIS OF PHOSPHATE-BASED INHIBITORS AND APPLICATIONS THEREOF

CROSS REFERENCE TO RELATED APPLICATION

This application claims filing benefit of U.S. Provisional Patent Application Ser. No. 62/928,727, having a filing date of Oct. 31, 2019, which is incorporated herein by reference in its entirety.

SEQUENCE LISTING

A Sequence Listing has been filed electronically in ASCII format and is hereby incorporated by reference in its entirety. Said ASCII copy, created on Nov. 6, 2020, is named USC-560_Sequence_List.txt and is 1,074 bytes in size.

BACKGROUND

Kinetoplastid parasites, such as *Trypanosoma cruzi* (*T. cruzi*), *Trypanosoma brucei* (*T. brucei*), and *Leishmania* spp. encompass various forms found in insect vectors (i.e., kissing bugs, tsetse flies, and sandflies) and are responsible for a number of serious diseases in both humans and animals. For instance, *T. cruzi* is the causative agent for Chagas' disease, which is estimated to affect approximately 6-7 million people worldwide, with most residing in 21 Latin American countries, and approximately 300,000 cases reported in the United States. *T. brucei* is the causative agent for human African sleeping sickness, and *Leishmania* spp. are protozoan parasites causing the disease Leishmaniasis.

Kinetoplastid parasites such as these utilize and depend on the pentose phosphate pathway (PPP) and glycolysis when metabolizing D-glucose. The PPP has both an oxidative branch and a non-oxidative branch and is utilized for production of the reducing agent NADPH and intermediates that are used in nucleic acid and nucleotide biosynthesis, as well as for cellular defenses against oxidative stress. Both the PPP and the glycolysis pathways are implicated as targets in the kinetoplastid parasites for anti-parasitic drug development, particularly *T. cruzi*.

Existing treatments in countering *T. cruzi* infections include benznidazole and nifurtimox, which are exceptionally efficacious during the acute stage of Chagas' disease but exhibit much lower efficacy during the chronic stage, though the reasons why are not well understood. There also exists tolerability problems from the usage of these medicines that cause poor patient compliance, with side effects including anorexia, vomiting, polyneuropathy, and allergic dermopathy. *T. brucei* is treated with various drugs including pentamidine, suramin, eflornithine, and melarsoprol. Medical intervention for treatment of Leishmaniasis requires treatment such as pentavalent antimony-based medicines, or more expensive treatments such as amphotericin B, miltefosine, or paromomycin.

*T. cruzi* ribose 5-phosphate isomerase type B (TcRPI-B) is an enzyme of the PPP that catalyzes the isomerization of ribose 5-phosphate (R5P) and ribulose 5-phosphate (Ru5P) in either a forward or reverse direction (FIG. 1). Type B RPIs are also found in protozoa and some bacteria. Mammalian genomes lack the type B RPI. Instead, mammalian genomes include the type A RPI and there is a significant structural divergence between the two enzyme classes. The essentiality of TcRPI-B remains to be determined; however, metabolic studies have demonstrated that *T. cruzi* trypomastigotes and amastigotes use D-glucose as their preferred carbon source in glucose-rich media, and D-glucose is the starting substrate of the PPP metabolic pathway. Thus, Type B RPI has been implicated as a drug target of interest for the early-stage drug development of Chagas' disease, as well as other diseases caused by kinetoplastid parasites.

A need exists for methods for facile methods for forming compounds that strongly bind to drug targets found in these parasites such as Type B RPI.

SUMMARY

According to one embodiment, disclosed is a one-step process for forming phosphate-based enzyme inhibitors, and in one particular embodiment, for forming phosphate-based inhibitors of enzymes of the protozoan pentose phosphate pathway. The process includes combining o-phosphorylethanolamine with an acyl chloride, e.g., a haloacetyl chloride, a phenyl acetyl chloride, etc., while maintaining the reaction at a pH of from 4 to about 6.

Also disclosed are methods for forming a pharmaceutical composition that can include forming a phosphate-based enzyme inhibitor by combining o-phosphorylethanolamine with a derivatized acyl chloride while maintaining the reaction at a pH of about 4 to about 6, and then combining the reaction product with a pharmaceutically acceptable carrier.

Also disclosed are phenyl-derivatized inhibitors as may be formed by the disclosed processes. A phenyl-derivatized inhibitor can have the following structure:

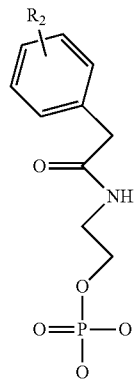

in which $R_2$ is hydrogen, halogen, C1-C4 alkyl halogen, C1-C4 alkyl, or C1-C4 alkoxy.

Pharmaceutical compositions, including the phenyl-derivatized inhibitors, and methods for treating an animal or human by use of the pharmaceutical compositions are also provided.

Other features and aspects of the present disclosure are discussed in greater detail below.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
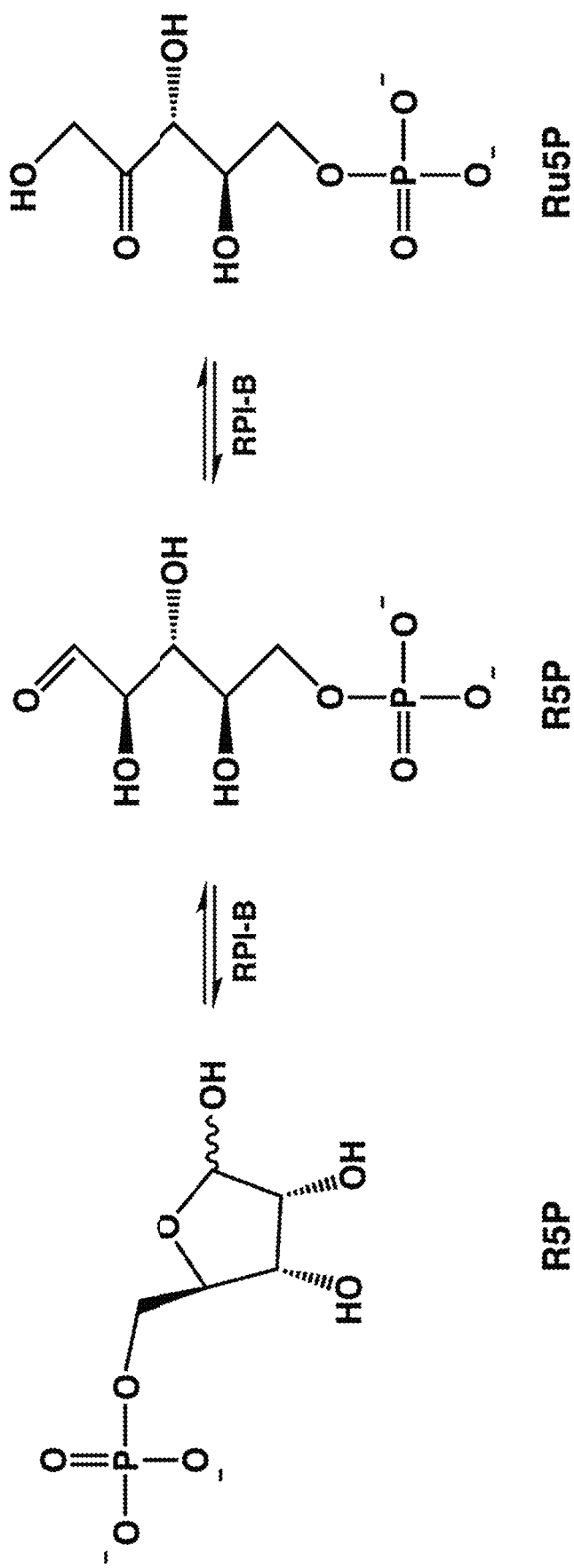
FIG. 1 illustrates the isomerization reaction between R5P and Ru5P as catalyzed by TcRPI-B.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is generally directed to a facile, one-step synthesis approach for forming phosphate-based enzyme inhibitors. In one embodiment, the methods can be used to form inhibitors of enzymes of the pentose phosphate pathway (PPP), and in one particular embodiment, to form inhibitors of enzymes of the PPP that are not normally produced by the mammalian genome, e.g., type B RPI. Inhibitors formed by disclosed methods can exhibit activity against other enzymes, however, and the function of inhibitors as may be formed according to disclosed methods are in no way limited to inhibition of non-mammalian enzymes or enzymes of the PPP. By way of example, and without limitations, other enzymes that inhibitors formed by disclosed methods can exhibit activity against can include other D-ribose-5-phosphate aldose-ketose isomerase enzymes in addition to type B RPI. Inhibitors formed by disclosed methods can also exhibit activity against enzymes of the D-ribulose-5-phosphate 3-epimerase class, such as ribulose 5-phosphate 3-epimerase (RPE).

Enzyme inhibitors formed by disclosed methods are phosphate-based inhibitors, similar to the known TcRPI-B inhibitors AlI6P and 4-phospho-D-erythronohydroxamic acid (4PEH) illustrated in FIG. 2 in the left panels. The right side of FIG. 2 illustrates several representative examples of phosphate-based inhibitors that can be formed by disclosed methods including Compound A (2-(2-phenylacetamido) ethyl dihydrogen phosphate), Compound B (2-(2-iodoacetamido)ethyl dihydrogen phosphate), Compound C (2-(2-bromoacetamido)ethyl dihydrogen phosphate), Compound D (2-(2-chloroacetamido)ethyl dihydrogen phosphate), and Compound E (2-(2-fluoroacetamido)ethyl dihydrogen phosphate).

Formation methods disclosed herein can include reaction of o-Phosphorylethanolamine (also commonly referred to as 2-Aminoethyl dihydrogen phosphate, o-Phosphocolamine, o-Phosphoethanolamine, or Colaminephosphoric acid) with an acyl chloride at acidic conditions. The acyl chloride reactant can include functionality that can be varied as desired. For instance, the acyl chloride can be a haloacetyl chloride, e.g., iodoacetyl chloride, bromoacetyl chloride, chloroacetyl chloride, fluoroacetyl chloride, or combinations thereof, and the formed phosphate-based inhibitors can be halogen containing compounds. The formation methods are not limited to formation of halogen containing compounds, however, and in other embodiments, the acyl chloride reactant can carry functionality other than or in addition to halogen.

A reaction scheme for forming an inhibitor according to disclosed methods can be as follows:

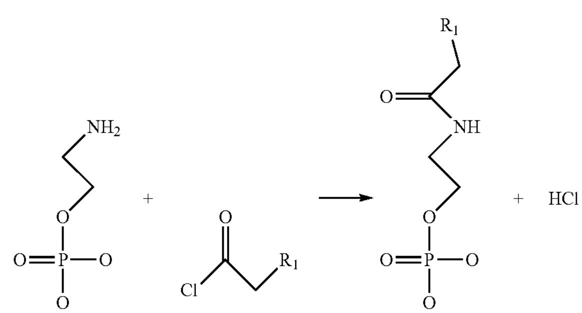

in which $R_1$ is halogen or a ring system including aryl and/or heterocyclic rings that are optionally derivatized with one or more of hydrogen, halogen, C1-C4 alkyl halogen, C1-C4 alkyl, or C1-C4 alkoxy.

In one embodiment, the acyl chloride can include a phenyl group and can have the following structure:

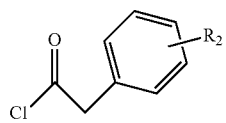

in which $R_2$ can be hydrogen, halogen, C1-C4 alkyl halogen, C1-C4 alkyl, or C1-C4 alkoxy.

The reaction of the acyl chloride and the o-phosphorylethanolamine can be carried out at somewhat acidic conditions, e.g., at a pH of about 4 to about 6, or at about pH 5 in some embodiments. To maintain the reaction at the desired reaction conditions as the reaction proceeds, a suitable base can be added, e.g., LiOH, NaOH, KOH, or the like.

Upon formation, according to the single-step reaction scheme, the product can be separated from the reaction mixture, e.g., by concentration in vacuo, and washed.

Figure 3:
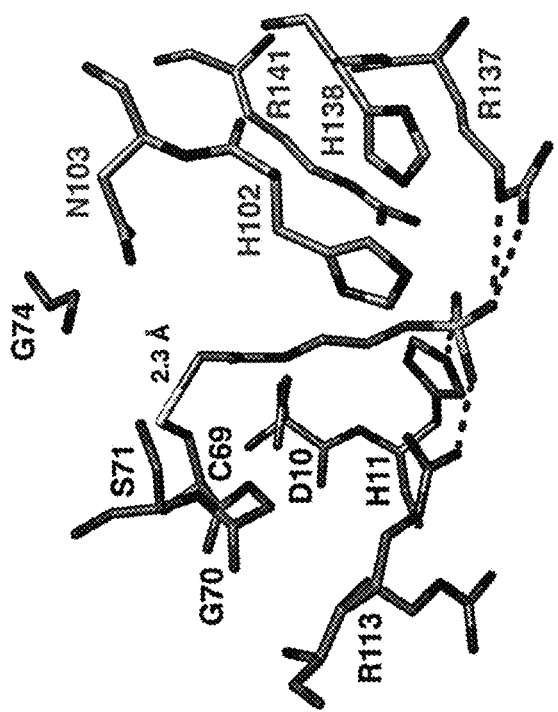
FIG. 3 illustrates substrate/inhibitor interactions in the active site of TcRPI-B and includes X-ray crystal structure of the TcRPI-B/R5P complex (PDB entry 3K7S) in the active site (left) (carbon atoms color-coded dark and light represent different subunits). In the center is illustrated a proposed reaction mechanism for the sulfur-carbon bond formation between the sulfhydryl group of TcRPI-B (C69) and an iodoacetamide moiety from Compound B of FIG. 2. A proposed irreversible complex of Compound B bound in the active site of TcRPI-B is shown on the right.
Figure 3:
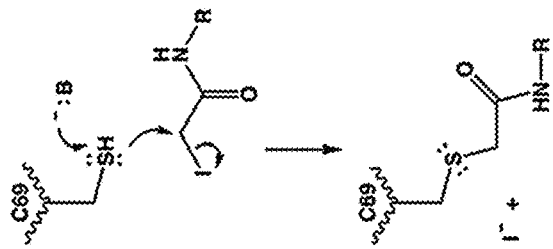
Figure 3:
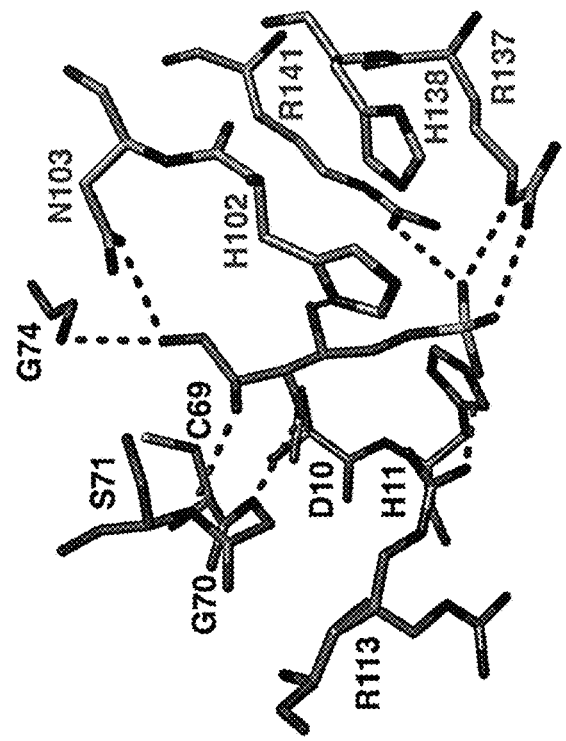

Without wishing to be bound to any particular theory, it is believed that inhibitors formed according to disclosed methods can interact with a sulfhydryl group of a targeted enzyme, for instance the sulfhydryl group of TcRPI-B (C69) as illustrated in the proposed reaction mechanism of FIG. 3 (center) between the iodoacetamide moiety of Compound B as described herein and TcRPI-B.

FIG. 3 (left) illustrates the X-ray crystal structure of the TcRPI-B/R5P complex (PDB entry 3K7S) in the active site as carried out in the PPP. On the right is illustrated a proposed complex of an inhibitor formed as described herein, and specifically, Compound B of FIG. 2 with the active site of TcRPI-B. As indicated, it is proposed that the inhibitor can form an irreversible complex with the active site, inhibiting activity of the enzyme for the PPP R5P↔Ru5P catalysis.

Methods for forming pharmaceutical compositions are also encompassed herein, as well as pharmaceutical compositions including inhibitors formed according to disclosed methods. Pharmaceutical compositions can by formed by combining a pharmaceutically acceptable carrier and at least one compound as disclosed herein in a pharmaceutically effective amount. In one embodiment, a pharmaceutical composition formation method can include formation of one of Compound A, B, C, D, or E, or a combination thereof as described.

The term "pharmaceutically effective amount" refers to the amount of a drug or pharmaceutical agent that will elicit the biological or medical response of a tissue, system, animal, or human that is being sought by a researcher or clinician. This amount can be a therapeutically effective amount.

The term "pharmaceutically acceptable carrier" is used herein to refer to a carrier that is useful in preparing a pharmaceutical composition that is generally safe, non-toxic, and neither biologically nor otherwise-undesirable, and is acceptable for veterinary use as well as human pharmaceutical use. A "pharmaceutically acceptable carrier" as used in the specification and claims can include both one and more than one such carrier. By "pharmaceutically acceptable," it is meant that the carrier must be compatible with the other ingredients of the formulation and not deleterious to the recipient thereof.

Pharmaceutical compositions may be prepared by any of the methods well known in the art of pharmacy. Pharmaceutical compositions encompass any compositions made by admixing the active ingredients and a pharmaceutically acceptable carrier. The carrier may take a wide variety of forms depending on the form of preparation desired for administration, e.g., oral or parenteral (including intravenous).

The terms "administration of" or "administering a" pharmaceutical composition should be understood to mean providing a pharmaceutical composition to an individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

Thus, the pharmaceutical composition can be formed as discrete units suitable for oral administration such as capsules, cachets, or tablets, each containing a predetermined amount of the active ingredients. Further, the composition can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the composition may also be administered by controlled release means and/or delivery devices. The foregoing list is illustrative only and is not intended to be limiting in any way.

Pharmaceutical compositions intended for oral use may contain one or more agents selected from the group consisting of sweetening agents, flavoring agents, coloring agents, and preserving agents in order to provide pharmaceutically elegant and palatable preparations. Tablets may contain a composition having at least one of the compounds described herein in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. A tablet may be prepared by compression or molding, optionally with one or more accessory ingredients or adjuvants. Compressed tablets may be prepared by compressing, in a suitable machine, at least one of disclosed compounds in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions for oral use may also be presented as hard gelatin capsules wherein one or more of the disclosed compounds is mixed with an inert solid diluent, for example, calcium carbonate, calcium phosphate or kaolin, or as soft gelatin capsules wherein the compound(s) is/are mixed with water or an oil medium, for example peanut oil, liquid paraffin, or olive oil.

Pharmaceutical compositions can also include aqueous suspensions, which contain the active materials in admixture with excipients suitable for the manufacture of aqueous suspensions. In addition, oily suspensions may be formulated by suspending at least one of the disclosed compounds in a vegetable oil, e.g., arachis oil, olive oil, sesame oil or coconut oil, or in a mineral oil such as liquid paraffin. Oily suspensions may also contain various excipients. The pharmaceutical composition may also be in the form of oil-in-water emulsions, which may also contain excipients such as sweetening and flavoring agents.

Pharmaceutical compositions can be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions can be in a form suitable for topical use, such as, for example, an aerosol, cream, ointment, lotion, dusting powder, or the like. Further, the compositions can be in a form suitable for use in transdermal devices. These formulations may be prepared via conventional processing methods. As an example, a cream or ointment can be prepared by mixing hydrophilic material and water, together with about 5 wt % to about 10 wt % of one or more of the disclosed compounds, to produce a cream or ointment having a desired consistency.

Pharmaceutical compositions can also be in a form suitable for rectal administration, wherein the carrier is a solid. Suitable carriers include cocoa butter and other materials commonly used in the art.

Methods are also provided for inhibiting a D-ribose-5-phosphate aldose-ketose isomerase and/or a D-ribulose-5-phosphate 3-epimerase, both in vitro and in vivo. In one embodiment, the method comprises contacting the enzyme with a compound having the following structure:

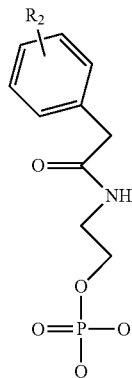

in which $R_2$ is hydrogen, halogen, C1-C4 alkyl halogen, C1-C4 alkyl, or C1-C4 alkoxy. One example of which is Compound A, 2-(2-phenylacetamido)ethyl dihydrogen phosphate.

For instance, a method is provided for inhibiting a D-ribose-5-phosphate aldose-ketose isomerase and/or a D-ribulose-5-phosphate 3-epimerase, for instance inhibiting type B RPI and/or RPE in a parasitic organism. This method comprises locating a compound as described or a composition including a compound as described in an area that includes the enzyme. For instance, a method can include administering to the parasitic organism a composition comprising a pharmaceutically acceptable carrier and at least one compound having the following structure:

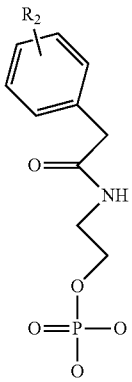

in which $R_2$ is hydrogen, halogen, C1-C4 alkyl halogen, C1-C4 alkyl, or C1-C4 alkoxy.

The parasitic organism can be a parasite that contains a D-ribose-5-phosphate aldose-ketose isomerase and/or a D-ribulose-5-phosphate 3-epimerase or can be an organism that carries the parasite. The parasitic organism can be a cause of a disease associated with the parasite. Such diseases include American Trypanosomiasis (Chagas' disease), Human African Trypanosomiasis (African Sleeping Sickness), Leishmaniasis, Malaria, Schistosomiasis (Snail Fever), Filarial diseases, etc.

Also, a method is provided for treating a mammal that is infected by a parasite or parasitic organism. This method comprises administering to the disease-affected mammal a composition comprising a pharmaceutically acceptable carrier and having the following structure:

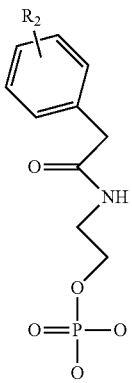

in which $R_2$ is hydrogen, halogen, C1-C4 alkyl halogen, C1-C4 alkyl, or C1-C4 alkoxy.

Examples of such disease-affected mammals include humans and domestic animals (e.g., dogs, cats, and thereof).

The term "treatment" or "treating" means any administration of a pharmaceutical composition to obtain a desired pharmacologic and/or physiologic effect. The effect may be prophylactic in terms of completely or partially preventing a disease or symptom thereof, and/or may be therapeutic in terms of a partial or complete cure for a disease and/or adverse effect attributable to the disease. Treatment includes (a) inhibiting the disease in the subject that is experiencing or displaying the pathology or symptomatology of the diseased (i.e., arresting further development of the pathology and/or symptomatology), or (b) ameliorating the disease in the subject that is experiencing or displaying the pathology or symptomatology of the diseased (i.e., reversing the pathology and/or symptomatology).

The present disclosure may be better understood with reference to the Examples, set forth below.

EXAMPLE

Materials and Methods

Starting materials were purchased from commercial sources and used as received. Oligonucleotide primers were from Gibco, Life Technologies, and deoxynucleoside-5_triphosphates (dNTPs) were from Promega. Restriction endonucleases were purchased from New England Biolabs. *E. coli* strain BL21 CodonPlus (DE3) was purchased from Stratagene. The HiTrap® Chelating High Performance columns were purchased from GE Healthcare. Dulbecco's Modified Eagle's medium (DMEM) was purchased from CellGro. Amphotericin B, chlorophenol red-β-D-galactoside (CPRG), cobalt-nitrilotriacetic acid (Co-NTA) resin, lysogeny broth (LB), lysozyme (type VI), kanamycin sulfate, protease inhibitor tablets (EDTA-free), and all other chemicals were purchased from Fisher Scientific. Ethylenediaminetetraacetic acid tetrasodium salt hydrate (>99.0%), imidazole (99+%), isopropyl-β-D-thiogalactopyranoside (IPTG), bovine pancreas deoxyribonuclease I (DNase I), bovine pancreas ribonuclease A (RNase A), chloramphenicol (water soluble), 4-(1,1,3,3-Tetramethylbutyl)phenyl-polyethylene glycol solution (Triton X-100 solution), phenylmethylsulfonyl fluoride (PMSF), and all buffer salts (≥98%) were purchased from Sigma-Aldrich. All chemicals and coupled enzymes used to determine TcRPI-B activity were also obtained from Sigma-Aldrich, with the exception of transketolase (TKT) and *T. cruzi* ribulose 5-phosphate 3-epimerase (TcRPE-1), which were obtained as the recombinant enzymes from *T. cruzi*.

Cloning of the TcRPI-B Gene. The TcRPI-B ORF (GenBank® accession code: DQ782334) of 480 bp was amplified by PCR from genomic DNA from *T. cruzi* CL-Brener clone epimastigotes. Primers were designed according to the sequence data obtained from the GenBank® database. NdeI and XhoI sites were included to facilitate the directional cloning into the expression vector. The sequences of the primers were as follows: sense primer TcRPIBFW: 5'-CATATGACGCGCCGAGTCG-3' (start bold, NdeI underlined) (SEQ ID NO: 1); antisense primer TcRPIBRV: 5'-CTCGAGCCTGTACATCATTTCTCG-3' (XhoI underlined) (SEQ ID NO: 2). PCR conditions were as follows: initial denaturation (300 seconds at 95° C.), 30 cycles of denaturation (30 seconds at 95° C.), annealing (30 seconds at 58° C.), elongation (60 seconds at 68° C.), and a final extension step (90 seconds at 68° C.). The PCR products were isolated from a 1% agarose gel, purified by the QIAquick PCR Purification Kit protocol (QIAGEN), and cloned into a pGEM®-T Easy Vector System (Promega). Sequencing of the product was performed using the sequencing service provided by MACROGEN (South Korea).

Construction of the Plasmid pET-22b(+)-TcRPI-B, Expression, and Purification of Recombinant TcRPI-B.

The TcRPI-B gene was excised as NdeI/XhoI fragments from the pGEM®-T Easy Vector System I, gel purified, and subcloned into the NdeI and XhoI sites of the pET-22b(+) expression vector (Novagen®). The resulting construct presenting a poly-His tag at the C-terminus was transferred to *Escherichia coli* BL21 CodonPlus DE3 cells. Transformation with pET-22b (+)-TcRPI-B was performed according to the procedures described in the instruction manual. For expression, a single colony was grown overnight at 37° C. in LB medium containing 50 µg/mL kanamycin and 10 µg/mL chloramphenicol. Cells were diluted 1:25 in LB medium containing antibiotics as described above and grown at 37° C. When an optical density of 0.6 at 600 nm was reached, isopropyl-β-D-thiogalactopyranoside (IPTG) was added to a final concentration of 0.5 mM to induce protein expression. Cell culture continued overnight at 18° C. with shaking at 250 rpm. Cells were harvested by centrifugation at 3,000×g for 10 minutes at 4° C. and resuspended in lysis buffer containing: 50 mM Tris-HCl (pH 7.5), 500 mM NaCl, 0.1% Triton™ X-100, 2 mM PMSF, and lysozyme at a final concentration of 1 mg/mL. DNA was digested by treatment with 0.1 mg/mL DNase I (final concentration). The cell-free extract was obtained by centrifugation at 20,000×g for 25 minutes at 4° C. The recombinant enzyme was purified through one step using a $Ni^{2+}$ resin (GE Healthcare) that was pre-equilibrated in a buffer containing 50 mM Tris-HCl (pH 7.6), 500 mM NaCl. The column was washed sequentially with 50 column volumes (CV) of the equilibration buffer and 50 CVs of the same buffer added with 50 mM imidazole. TcRPI-B was eluted with 2 CVs of the equilibrium buffer added with 300 mM imidazole and 500 µL fractions were collected. All purification procedures were performed at 4° C. and the elution profile was monitored by enzymatic activity. Purity of the recombinant TcRPI-B was analyzed by SDS-PAGE followed by Coomassie® Blue staining. The eluted fractions were then pooled and desalted by following the PD-10 desalting column protocol (GE Healthcare) that used equilibrium buffer as the desalting buffer.

Reactions were monitored by LC-MS (2.6 mm C18 50×2.10 mm column). Spectra of $^1H$, $^{13}C$, and $^{31}P$ NMR were obtained on a 400 MHz instrument in $D_2O$ unless otherwise noted. Chemical shifts were reported in parts per million with the residual solvent peak used as an internal standard ($D_2O$=4.79 ppm for $^1H$). $^1H$ NMR spectra were run at 400 MHz and are tabulated as follows: chemical shift, multiplicity (s=singlet, d=doublet, t=triplet, q=quartet, p=pentet, m=multiplet, bs=broad singlet, dt=doublet of triplet, tt=triplet of triplet), number of protons, and coupling constant(s). $^{13}C$ NMR spectra were run at 100 MHz using a proton-decoupled pulse sequence with a d1 of 1 second unless otherwise noted and are tabulated by observed peak. $^{31}P$ NMR spectra were run at 160 MHz and tabulated by observed peak. High-resolution mass spectra were obtained on an ion trap mass spectrometer using heated electrospray ionization (HESI).

Figure 2:
FIG. 2 includes open-chain forms of the TcRPI-B inhibitors AlI6P ($K_i$=15 mM) and 4-phospho-D-erythronohydroxamic acid (4PEH) ($K_i$=1.2 mM) and the structure of Compounds A-E formed according to methods as described herein.
Figure 2:
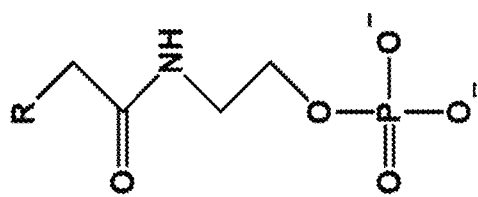
Figure 2:
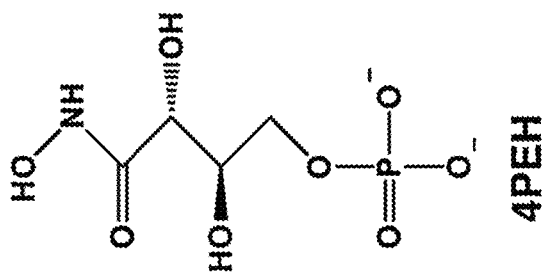
Figure 2:
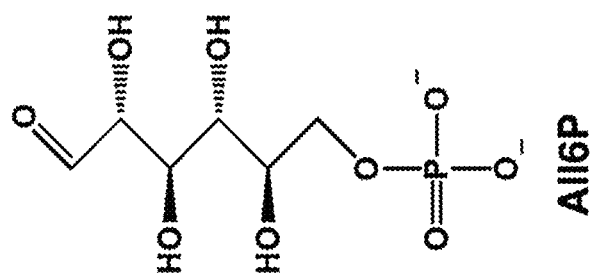

Sample Preparation, Trypsin Digestion LC/MSMS, and Data Analysis of TcRPI-B Exposed to Compound B (FIG. 2).

Sample preparation: Purified TcRPI-B was buffer exchanged into 50 mM ammonium bicarbonate (pH 8.0) by using a PD-10 desalting column (GE Life Sciences). The concentration of TcRPI-B was adjusted to 100 µM for the monomer [TcRPI-B: M.W.=19,816 g/mol; $\varepsilon_{280}$=5,120 M$^{-1}$ cm$^{-1}$] using an Agilent 8453 UV-Visible spectrophotometer. A protein test sample was incubated with compound B (FIG. 2) at a final concentration of 500 µM at 4° C. for 30 minutes and a control sample was prepared that was in the absence of compound B. Samples to be analyzed by LC/MSMS were first quantitated for protein content using a Pierce™ bicinchoninic acid (BCA) Protein Assay Kit and normalized to 50 µg of protein by diluting the appropriate amount of sample in 50 mM ammonium bicarbonate. Normalized samples were digested with trypsin at a 50:1 protein:trypsin concentration. Samples were incubated for 4 hours and then aliquoted for LC-MS analysis.

Nanoflow LC: Chromatographic separation was achieved using a Thermo Scientific™ EASY-nLC™ 1200 system (Bremen, Germany). Pico-frit columns were purchased from New Objective (Woburn, Mass.) and bomb packed to a length of 20-30 cm with reverse phase ReproSil-Pur® 120 Å C18-AQ 3 µm particles (Dr. Maisch, Germany). The sample, as a volume of 2.0 µL, was injected and subsequently separated using a gradient of mobile phase A (98% water, 2% acetonitrile, and 0.1% formic acid) and mobile phase B (80% acetonitrile, 20% water, and 0.1% formic acid). The LC method consisted of a 120-minute gradient with a linear ramp from 0% B to 40% B, a 1-minute ramp to 100% B, which was held for 6 minutes (123-129 minutes), followed by equilibration of the column at 0% B (130-140); a flow rate of 300 nL/min was used.

Mass Spectrometry: Orbitrap tandem mass spectrometry was performed using a Thermo Scientific™ Q Exactive™ HF (Bremen, Germany) in a top 20 data dependent acquisition (DDA) mode, where the 20 most abundant precursors were selected for fragmentation per full scan. MS1 and MS2 scans were performed at a resolving power of 120,000 and 15,000 at m/z 200, respectively. A dynamic exclusion window of 20 seconds was used to avoid repeated interrogation of abundant species. Automatic gain control (AGC) was 1e6 and 1e5 for MS1 and MS2 scans, respectively. Samples were run in random order, and a quality control BSA digest was run every fifth injection to ensure proper LC-MS/MS reproducibility.

Data Analysis: Resulting raw data were loaded into Proteome Discoverer™ (version 1.4). Spectrum files were run through the spectrum selector node to appropriately identify peaks and this data was collated using the SEQUEST HT node and aligned with a FASTA file that contained Ribose 5-phosphate isomerase. A custom modification was created within Proteome Discoverer™ to account for the covalent inhibitor modification. Methionine oxidation (dynamic) modifications were also considered in SEQUEST HT with a maximum of 2 potential missed cleavage sites and peptide lengths between 6 and 144 amino acids.

Compound A (2-(2-phenylacetamido)ethyl dihydrogen phosphate)

o-Phosphorylethanolamine (140 mg, 1.0 mmol) was dissolved in deionized water (1.0 mL) at room temperature. The pH was adjusted to ~5 with the dropwise addition of 5 M LiOH (0.5 mL) and was allowed to stir for 30 minutes. Phenylacetyl chloride (0.39 mL, 2.5 mmol) was added dropwise while maintaining the pH at ~5 with the dropwise addition of 5 M LiOH. The reaction mixture was then concentrated in vacuo, leaving a white powder. The resulting white powder was then washed with diethylether (Et$_2$O) (3×10 mL) and then ethanol (15 mL). The resulting white powder was placed in a −30° C. refrigerator for 30 minutes and then lyophilized for 24 hours to yield 83 mg (32% yield) of compound A as a white powder. $^1$H NMR (400 MHz, D$_2$O): δ=7.43-7.34 (m, 5H), 3.86 (q, J=5.8 Hz, 2H), 3.65 (s, 2H), 3.39 (t, J=5.4 Hz, 2H); $^{13}$C NMR (100 MHz, D$_2$O): δ=175.0, 135.2, 129.3, 129.0, 127.4, 63.2, 42.4, 40.6; $^{31}$P NMR (160 MHz, D$_2$O): δ=3.97, 2.88; HRMS (ESI) m/z calculated for C$_{10}$H$_{14}$NO$_5$P [M+H]$^+$: 260.06824, found: 260.06790.

Compound B (2-(2-iodoacetamido)ethyl dihydrogen phosphate)

o-Phosphorylethanolamine (140 mg, 1.0 mmol) was dissolved in deionized water (1.0 mL) at room temperature. The pH was adjusted to ~5 with the dropwise addition of 5 M LiOH (0.5 mL) and was allowed to stir for 30 minutes. Iodoacetyl chloride (0.39 mL, 2.5 mmol) was added dropwise while maintaining the pH at ~5 with the dropwise addition of 5 M LiOH. The reaction mixture was then concentrated in vacuo, leaving a white powder. The resulting white powder was then washed with Et$_2$O (3×10 mL) and then ethanol (15 mL). The resulting white powder was placed in a −30° C. refrigerator for 30 minutes and then lyophilized for 24 hours to yield 180 mg (58% yield) of compound B as a white powder. 1H NMR (400 MHz, D2O): δ=3.78 (m, 2H), 3.74 (s, 2H), 3.33 (t, J=5.4 Hz, 2H); 13C NMR (100 MHz, D2O): δ=172.2, 62.0, 41.4, 2.0; 31P NMR (160 MHz, D2O): δ=4.89; HRMS (ESI) m/z calculated for C4H9INO5P [M+Na]+: 309.94140, found: 309.93336.

Compound C (2-(2-bromoacetamido)ethyl dihydrogen phosphate)

o-Phosphorylethanolamine (140 mg, 1.0 mmol) was dissolved in deionized water (1.0 mL) at room temperature. The pH was adjusted to ~5 with the dropwise addition of 5 M LiOH (0.5 mL) and was allowed to stir for 30 minutes. Bromoacetyl bromide (0.39 mL, 2.5 mmol) was added dropwise while maintaining the pH at ~5 with the dropwise addition of 5 M LiOH. The reaction mixture was then concentrated in vacuo, leaving a white powder. The resulting white powder was then washed with Et$_2$O (3×10 mL) and then ethanol (15 mL). The resulting white powder was placed in a −30° C. refrigerator for 30 minutes and then lyophilized for 24 hours to yield 130 mg (49% yield) of compound C as a white powder. $^1$H NMR (400 MHz, D$_2$O): δ=3.89 (s, 2H), 3.79 (m, 2H), 3.39 (t, J=5.5 Hz, 2H); $^{13}$C NMR (100 MHz, D$_2$O): δ=170.0, 62.4, 40.8, 28.0; $^{31}$P NMR (160 MHz, D$_2$O): δ=2.44; HRMS (ESI) m/z calculated for C$_4$H$_9$BrNO$_5$P [M+H]$^+$: 283.92939, found: 283.92924.

Compound D (2-(2-chloroacetamido)ethyl dihydrogen phosphate)

o-Phosphorylethanolamine (140 mg, 1.0 mmol) was dissolved in deionized water (1.0 mL) at room temperature. The pH was adjusted to ~5 with the dropwise addition of 5 M LiOH (0.5 mL) and was allowed to stir for 30 minutes. Chloroacetyl chloride (0.39 mL, 2.5 mmol) was added dropwise while maintaining the pH at ~5 with the dropwise addition of 5 M LiOH. The reaction mixture was then concentrated in vacuo, leaving a white powder. The resulting white powder was then washed with Et$_2$O (3×10 mL) and then ethanol (15 mL). The resulting white powder was placed in a −30° C. refrigerator for 30 minutes and then lyophilized for 24 hours to yield 180 mg (81% yield) of compound D as a white powder. $^1$H NMR (400 MHz, D$_2$O): δ=4.11 (s, 2H), 3.79 (q, J=5.9 Hz, 2H), 3.41 (t, J=5.5 Hz, 2H); $^{13}$C NMR (100 MHz, D$_2$O): δ=169.4, 62.1, 42.4, 41.1; $^{31}$P NMR (160 MHz, D$_2$O): δ=5.02; HRMS (ESI) m/z calculated for C$_4$H$_9$ClNO$_5$P [M+Na]$^+$: 239.97991, found: 239.97979.

Compound E (2-(2-fluoroacetamido)ethyl dihydrogen phosphate)

o-Phosphorylethanolamine (140 mg, 1.0 mmol) was dissolved in deionized water (1.0 mL) at room temperature. The pH was adjusted to ~5 with the dropwise addition of 5 M LiOH (0.5 mL) and was allowed to stir for 30 minutes. Fluoroacetyl chloride (0.39 mL, 2.5 mmol) was added dropwise while maintaining the pH at ~5 with the dropwise addition of 5 M LiOH. The reaction mixture was then concentrated in vacuo, leaving a white powder. The resulting white powder was then washed with Et$_2$O (3×10 mL) and then ethanol (15 mL). The resulting white powder was placed in a −30° C. refrigerator for 30 minutes and then lyophilized for 24 hours to yield 160 mg (78% yield) of compound E as a white powder. $^1$H NMR (400 MHz, D$_2$O): δ=4.72-4.60 (d, J=47.6, 2H), 3.93 (m, 2H), 3.17 (m, 2H); $^{13}$C NMR (100 MHz, D$_2$O): δ=176.2, 78.3, 60.1, 40.5; $^{31}$P NMR (160 MHz, D$_2$O): δ=4.98; HRMS (ESI) m/z calculated for C$_4$H$_9$FNO$_5$P [M−H]$^−$: 200.01296, found: 200.01286.

Results

TcRPI-B Enzyme—Inhibitor Assays

The activity of TcRPI-B was determined by a coupled enzyme assay following consumption of NADH at 340 nm, at 30° C., in a Beckman Coulter DU®600 Spectrophotometer, using a mixture containing 50 mM triethanolamine (pH 7.5), 5 mM MgCl$_2$, 3 mM NADH, 0.025 mM thiamine pyrophosphate, 1 unit of transketolase (EC 2.2.1.1), 1 unit of ribulose 5-phosphate 3-epimerase (EC 5.1.3.1), 20 units of triosephosphate isomerase (EC 5.3.1.1), 2 units of α-glycerophosphate dehydrogenase (EC 1.1.1.8), and 2 mM R5P for the screening of the inhibitors. For the determination of $K_i$, the concentration of R5P was 0.4 mM, 0.8 mM, and 2.0 mM.

Figure 4:
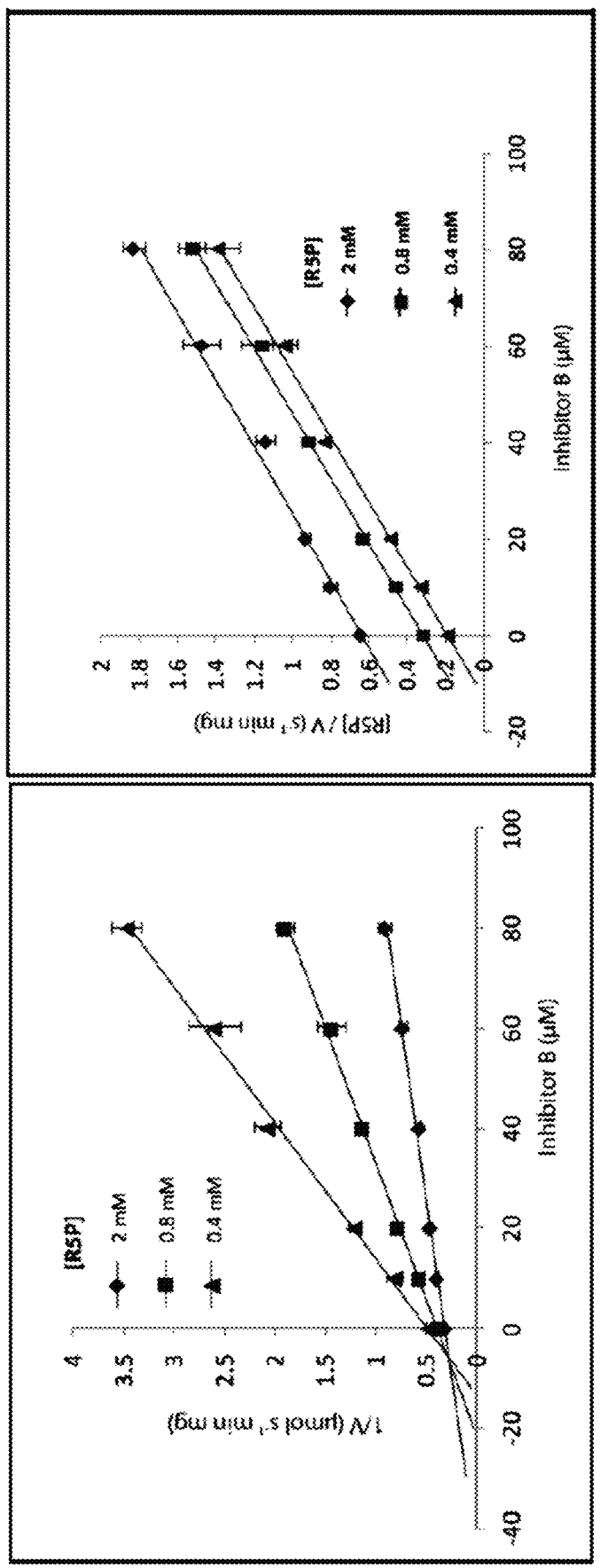
FIG. 4 illustrates the kinetics of inhibition of TcRPI-B by Compound B of FIG. 2. On the left is provided Dixon plots of 1/V as a function of the concentration of Compound B ([B]) to determine the value of the inhibition constant ($K_i$) for Compound B. The value calculated from the extrapolation of the intersection of the three lines with the x-axis was 5.5±0.1 μM (mean of four independent experiments). On the right is provided a plot of [R5P]/V vs. [B], to determine the type of inhibition for Compound B. Since the three lines were observed to be parallel, the inhibition was concluded as competitive inhibition. The inhibitor concentrations assayed were 0, 10, 20, 40, 60, and 80 μM, at three concentrations of R5P (0.4, 0.8, and 2 mM). One of four independent experiments are shown in the panels. The experimental points shown are the mean of two determinations.

The activity of TcRPE-1 was determined in the same reaction mixture, without TcRPI-B, and replacing R5P by 4 mM ribulose 5-phosphate (Ru5P). Since the commercial R5P (Sigma-Aldrich) was found to be contaminated with Ru5P, the reaction mixtures without the addition of TcRPI-B were pre-incubated for 20 minutes at 30° C. in a closed tube; preliminary experiments showed that this was enough to eliminate the contaminating Ru5P. The reaction was started with the addition of TcRPI-B and further incubated for 10 minutes in the same tube, to surpass the lag observed with the recombinant RPI, and then the mixture was transferred to the spectrophotometer cuvette and the linear part of the progress curve was registered for 15 minutes. The screening of the inhibitors was performed using them at 0, 0.2, 0.5, 1.0 and 2.0 mM for both enzymes, TcRPI-B and TcRPE-1, and for the $K_i$ determination for compound B (FIG. 4) the concentrations used were: 0, 10, 20, 40, 60 and 80 μM, at each R5P concentration used.

Table 1, below, provides the effect of the five different compounds over TcRPI-B activity. The percentages of activity shown in the table are the mean of three determinations±standard deviation (SD).

TABLE 1

| Concentration (mM) | Compound A | Compound B | Compound C | Compound D | Compound E |
| --- | --- | --- | --- | --- | --- |
| 0.2 | 98.1 ± 3.2 | 25.2 ± 3.5 | 78.5 ± 4.8 | 107 ± 9 | 994 ± 107 |
| 0.5 | 97.4 ± 0.5 | 7.5 ± 3.9 | 62.7 ± 5.9 | 105 ± 7 | 2042 ± 686 |
| 1.0 | 95.3 ± 4.2 | 1.2 ± 0.3 | 41.3 ± 2.7 | 98.5 ± 2.1 | 3194 ± 921 |
| 2.0 | 89.2 ± 3.5 | 0.0 ± 0.0 | 18.3 ± 2.5 | 83.7 ± 8.9 | 2718 ± 269 |

Table 2, below, provides the effect of the five different compounds over TcRPE-1 activity. The percentages of activity shown in the table are the mean of three determinations±SD.

TABLE 2

| Concentration (mM) | Compound A | Compound B | Compound C | Compound D | Compound E |
| --- | --- | --- | --- | --- | --- |
| 0.2 | 100 ± 5 | 89.5 ± 4 | 91.1 ± 5.1 | 100 ± 6 | 111 ± 10 |
| 0.5 | 91.9 ± 4.3 | 89.5 ± 4 | 85.8 ± 4.4 | 103 ± 5 | 103 ± 7 |
| 1.0 | 87.4 ± 3.1 | 103 ± 5 | 77.3 ± 7.5 | 95.5 ± 7.9 | 93.2 ± 11.1 |
| 2.0 | 85.9 ± 4.4 | 57.4 ± 0.4 | 65.1 ± 5.2 | 82.6 ± 12 | 83.5 ± 9.7 |

Figure 5:
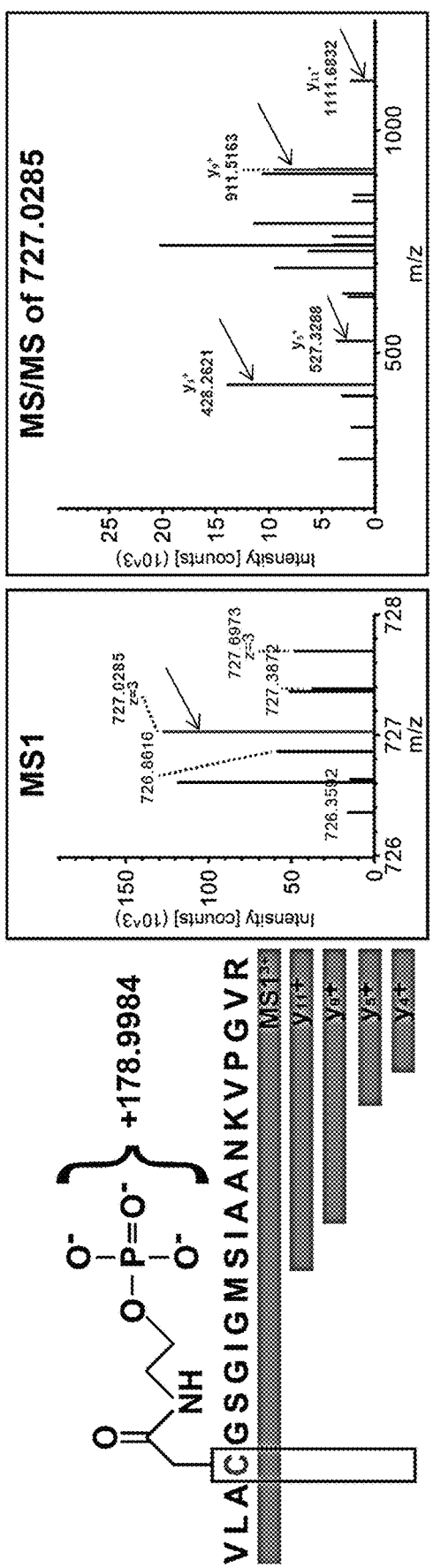
FIG. 5 provides the tandem mass spectrum of a peptide from TcRPI-B (residues V66-R86; SEQ ID NO: 3) that is labeled to Cys-69 by compound B (left panel). The MS1-ion that is labeled by the inhibitor lacking the iodine atom (+178.9984 Da) is marked with an arrow with mass shown (middle panel). The unlabeled y-ions are marked with an arrow and masses are shown (right panel). All unlabeled y-ions have a +1 charge and the MS1 ion has a +3 charge.

FIG. 5 shows TcRPI-B that underwent a trypsin digestion after being exposed to Compound B. The resultant enzymatic digestion was analyzed by LC/MSMS. Protein segment [V66-R86] of FIG. 5 shows an $MS1^{3+}$ mass spectrum, which includes the inhibitor, compound B, bound irreversibly to C69 (color coded). The portion of the inhibitor that linked onto C69 has a molecular mass of 178.9984 g/mol; also, this portion of the inhibitor lacks the iodine atom. The $MS1^{3+}$ peak appears in the mass spectrum at 727.0285, which includes residue segment V66-R86 and the bound inhibitor portion. Other protein segments appeared in the mass spectrum analysis that did not include the bound inhibitor, such as the $y_4^+$ [protein segment: P83-R86], $y_5^+$ [protein segment: V82-R86], $y_9^+$ [protein segment: A78-R86], and $y_{11}^+$ [protein segment: S76-R86]. The following masses were detected: 428.2621 for $y_4^+$, 527.3288 for $y_5^+$, 911.5163 for $y_9^+$, and 1111.6832 for $y_{11}^+$.

Biological Assays

Figure 6:
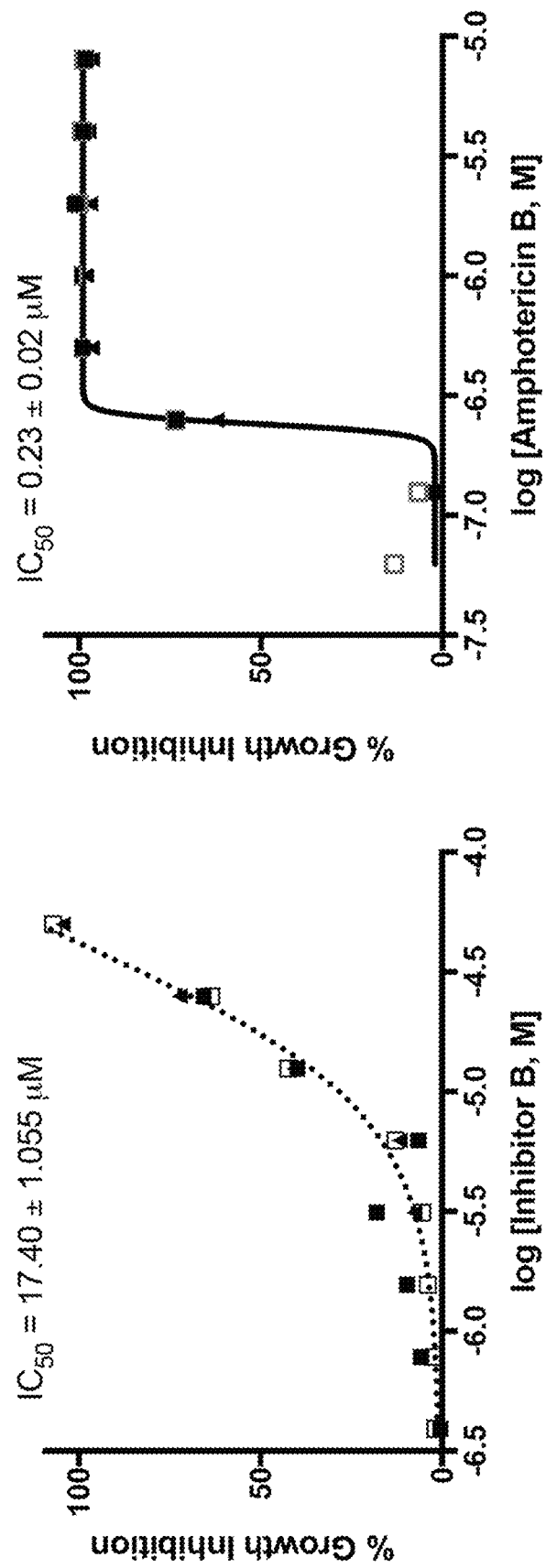
FIG. 6 presents dose response curves for the irreversible TcRPI-B inhibitor, Compound B activity (left) and Amphotericin B activity (right) on *T. cruzi* (Tulahuen strain) intracellular amastigote growth inhibition in NIH-3T3 fibroblasts. The curve and the $IC_{50}$ were calculated from measurements determined in triplicate and expressed as the % inhibition of parasite growth at each concentration.

General methods as known in the art were used for the IC50 determination involving in vitro preparation of cell cultures in mammalian cells and parasites, in addition to the treatment of *T. cruzi* amastigotes (Tulahuen strain) in NIH-3T3 fibroblasts with inhibitors. LLC-MK2 cells and NIH-3T3 fibroblast cells were incubated in DMEM that lacked phenol red and was supplemented with 10% fetal bovine serum (FBS) and penicillin-streptomycin-L-glutamine (PSG) [100 U/mL penicillin, 0.1 mg/mL streptomycin, and 0.292 mg/mL L-glutamine]. The incubation environment included 5% $CO_2$, was humidified, and the temperature was maintained at 37° C. Note: the concentration of D-glucose in DMEM was 4.5 g/L. *T. cruzi* parasites (Tulahuen strain) involved in the expression of the β-galactosidase gene (clone C4) were continuously cultured through infection of LLC-MK2 cells every 5-6 days in DMEM lacking phenol red and supplemented with 2% FBS and 1% PSG in a humidified environment containing 5% $CO_2$ at 37° C. In the colorimetric assay, phenol red was excluded because it would cause an interference by absorbing light at 590 nm. On days 5-7, trypomastigotes were harvested from the culture medium, which was achieved by first centrifuging the culture medium at 1,250 g for 7 minutes and allowing the trypomastigotes to swim away from the cell pellet (LLC-MK2 cells) in a 4-hour period; the supernatant containing trypomastigotes was collected. Since amastigotes lack the kind of mobility observed in trypomastigotes, this feature permitted a method of separating the two life-stage forms. During the interim period, a 96-well microtiter plate had wells filled with 100 μL of NIH-3T3 fibroblasts ($5 \times 10^4$ cells/well), and the mammalian cells were allowed to incubate for 3 hours for the purpose of attachment. In experiments involving a single-dose of an inhibitor, the final assay concentration for the compound was set to 80 μM. In experiments involving IC50 determinations, the TcRPI-B inhibitors were prepared as 10 mM stock solutions in 100% DMSO, and for each inhibitor, working concentrations ranged from 0-50 μM and were added to NIH-3T3 cells. Amphotericin B was used as a positive control (prepared as a 270 μM stock solution) and had a working concentration of 4 μM. Positive and negative controls were used for all 96-well plates. The controls included (i) fibroblasts and parasites, (ii) fibroblasts lacking parasites, and (iii) only the culture medium. A volume of 100 μL containing trypomastigotes ($5 \times 10^4$ cells/well) in DMEM lacking phenol red supplemented with 2% FBS and 1% PSG was transferred into each well followed by a 96-hour incubation. For color development, 50 μL of substrate solution [500 μM CPRG, 0.5% detergent NP40, and phosphate buffered saline (PBS)] was added per well and was allowed to incubate at 37° C. for 4 hours followed by measuring the absorbance at 590 nm using a PerkinElmer VICTOR™ 3X Reader. Absorbance values were proportional to parasite cell viability and the IC50 determinations were made through GraphPad Prism. All IC50 measurements were performed in triplicate. Results are illustrated in FIG. 6.

While certain embodiments of the disclosed subject matter have been described using specific terms, such description is for illustrative purposes only, and it is to be understood that changes and variations may be made without departing from the spirit or scope of the subject matter.

What is claimed is:

1. A method for forming a phosphate-based enzyme inhibitor, the method comprising:
combining o-phosphorylethanolamine with phenylacetyl chloride having the following structure:

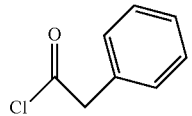

to form a reaction mixture; and
maintaining the reaction mixture at a pH of from about 4 to about 6, wherein the phosphate-based enzyme inhibitor is a D-ribose-5-phosphate aldose-ketose isomerase inhibitor and/or a D-ribulose-5-phosphate 3-epimerase inhibitor.

2. The method of claim 1, wherein the step of maintaining the reaction mixture at a pH of from about 4 to about 6 comprises adding a base to the reaction mixture.

3. A method for forming a pharmaceutical composition comprising
combining the phosphate-based enzyme inhibitor of claim 1 with a pharmaceutically acceptable carrier.

4. The method of claim 3, wherein the method comprises forming the pharmaceutical composition as discrete units.

5. The method of claim 3, further comprising combining the phosphate-based enzyme inhibitor with a sweetening agent, a flavoring agent, a coloring agent, or a preserving agent.

6. The method of claim 3, further comprising combining the phosphate-based enzyme inhibitor with an inert solid diluent.

7. The method of claim 3, wherein the pharmaceutical composition is in the form of a suspension, an aerosol, a cream, an ointment, a lotion, or a powder.

8. A pharmaceutical composition comprising:
a phosphate-based enzyme inhibitor having the following structure:

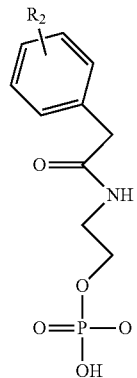

in which $R_2$ is hydrogen, halogen, C1-C4 alkyl halogen, C1-C4 alkyl, or C1-C4 alkoxy; and
a pharmaceutically acceptable carrier.

9. The pharmaceutical composition of claim 8, wherein the enzyme inhibitor comprises 2-(2-phenylacetamido)ethyl dihydrogen phosphate.

10. A method of inhibiting a D-ribose-5-phosphate aldose-ketose isomerase and/or a D-ribulose-5-phosphate 3-epimerase comprising locating the pharmaceutical composition of claim 8 in an area comprising a D-ribose-5-phosphate aldose-ketose isomerase and/or a D-ribulose-5-phosphate 3-epimerase.

11. The method of claim 10, wherein the method inhibits type B *T. cruzi* ribose 5-phosphate isomerase type B and/or ribulose 5-phosphate 3-epimerase.

12. The method of claim 10, wherein the area comprises a parasitic organism, the parasitic organism carrying the D-ribose-5-phosphate aldose-ketose isomerase and/or a D-ribulose-5-phosphate 3-epimerase.

* * * * *